| United States Patent [19] | [11] 3,932,652 |
|---|---|
| Haefely | [45] Jan. 13, 1976 |

[54] ANTIDEPRESSANT COMPOSITIONS
[75] Inventor: Willy Haefely, Reinach, Switzerland
[73] Assignee: Hoffmann-La Roche Inc., Nutley, N.J.
[22] Filed: Feb. 27, 1975
[21] Appl. No.: 553,781

Related U.S. Application Data
[63] Continuation-in-part of Ser. No. 371,441, June 19, 1973, abandoned.

[30] Foreign Application Priority Data
June 30, 1972 Switzerland.......................... 9846/72

[52] U.S. Cl................................ 424/274; 424/324
[51] Int. Cl.² ................. A61K 31/40; A61K 31/165
[58] Field of Search..................... 424/319, 274, 324

[56] References Cited
UNITED STATES PATENTS
3,701,829  10/1972  Bartholive........................... 424/319

OTHER PUBLICATIONS

Page, Scientific American, Vol. 197, No. 6, Dec. 1957.

Primary Examiner—Stanley J. Friedman
Attorney, Agent, or Firm—Samuel L. Welt; Jon S. Saxe; R. Hain Swope

[57] ABSTRACT

Pharmaceutical compositions active in the therapeutic treatment of depression and insomnia and containing a synergistic mixture of L-5-hydroxy-tryptophan or a pharmaceutically acceptable salt thereof and $N^1$-(D,L-seryl)-$N^2$-(2,3,4-trihydroxybenzyl)-hydrazine or a pharmaceutically acceptable salt thereof are disclosed.

10 Claims, No Drawings

ANTIDEPRESSANT COMPOSITIONS

RELATED APPLICATIONS

This application is a continuation-in-part of U.S. Pat. application Ser. No. 371,441 filed June 19, 1973, now abandoned.

BACKGROUND OF THE INVENTION

L-5-hydroxy-tryptophan is a known compound possessing utility in the symptomatic treatment of neurotic and psychotic disturbances wherein the depressive syndrome is manifest. The compound has also been found to possess sedative activity and is therefore also useful in relieving insomnia. L-5-hydroxy-tryptophan however, to be effective in alleviating the symptoms of mental depression must be administered in high dosages, i.e., up to 3 grams or more daily. Such high dosages of L-5-hydroxy-tryptophan have given rise to various undesirable side effects such as, for example, high blood pressure and gastrointestinal complaints which can become sufficiently serious so as to force discontinuance of the medication. It is therefore readily apparent that it would be advantageous to provide a means whereby the dosage of L-5-hydroxy-tryptophan required to achieve the desired therapeutic effect could be materially reduced. Such a reduction in dose would also reduce the undesirable side effects often associated with present dosage levels. Such means are provided in accordance with the present invention by the discovery of synergistic compositions whereby the desired therapeutic effect of L-5-hydroxy-tryptophan can be obtained with a materially reduced dosage. Further, the compositions of the present invention facilitate the therapeutic utilisation of L-5-hydroxy-tryptophan while substantially eliminating the undesirable side effects associated therewith.

BRIEF SUMMARY OF THE INVENTION

Therapeutically active antidepressant compositions comprising L-5-hydroxytryptophan or a pharmaceutically acceptable salt thereof and $N^1$-(D,L-seryl)-$N^2$-(2,3,4-trihydroxybenzyl)-hydrazine or a pharmaceutically acceptable salt thereof.

DETAILED DESCRIPTION OF THE INVENTION

The therapeutic compositions of the present invention comprise, as the active ingredient, a combination of L-5-hydroxy-tryptophan or a pharmaceutically acceptable salt thereof and $N^1$-(D,L-seryl)-$N^2$-(2,3,4-trihydroxybenzyl)-hydrazine or a pharmaceutically acceptable salt thereof, and a pharmaceutically acceptable, therapeutically inert carrier therefor. More specifically, the active ingredient of the compositions of the invention comprises from about one part to about two parts by weight L-5-hydroxy-tryptophan or the equivalent amount of a pharmaceutically acceptable salt thereof and from about one part to about five parts by weight $N^1$-(D,L-seryl)-$N^2$-(2,3,4-trihydroxybenzyl)-hydrazine or the equivalent amount of a pharmaceutically acceptable salt thereof.

As used herein, the expression "pharmaceutically acceptable salt" indicates salts with pharmaceutically acceptable acids or bases. In the case of L-5-hydroxy-tryptophan such salts may be salts formed with pharmaceutically acceptable bases, particularly strong bases such as, for example, sodium potassium or ammonium hydroxide as well as conventional salts formed with pharmaceutically acceptable organic and inorganic acids. Examples of suitable inorganic acids include hydrochloric acid, hydrobromic acid, phosphoric acid and the like and organic acids include, for example, maleic acid, oxalic acid, tartaric acid and the like. Suitable salts of the $N^1$-(D,L-seryl)-$N^2$-(2,3,4-trihydroxybenzyl)-hydrazine are acid addition salts formed with pharmaceutically acceptable organic or inorganic acids. Examples of suitable salts formed with inorganic acids include those formed with hydrochloric acid, hydrobromic acid, sulfuric acid, nitric acid, phosphoric acid and the like. Suitable salts with organic acids include those formed with acetic acid, benzoic acid, lactic acid, malic acid, maleic acid, salicyclic acid and the like. Of these, the preferred acid addition salt is the hydrochloride.

The compositions of the present invention are prepared simply by admixing L-5-hydroxy-tryptophan or a pharmaceutically acceptable salt thereof and $N^1$-(D,L-seryl)-$N^2$-(2,3,4-trihydroxybenzyl)-hydrazine or a pharmaceutically acceptable salt thereof. This mixture is ultimately embodied into a suitable enteral or parenteral dosage form. For example, the compositions can be compressed by conventional methods into tablets or filled into hard shell capsules. Further, the composition may also be enterally administered in the form of suppositories, solutions, syrups, suspensions and the like. In addition, the composition of the invention can be formulated into suitable dosage forms for parenteral administration which are prepared by methods well known in the art.

In addition to the active ingredient which comprises the combination of L-5-hydroxy-tryptophan and $N^1$-(D,L-seryl)-$N^2$-(2,3,4-trihydroxybenzyl)-hydrazine or their pharmaceutically acceptable salt, the compositions of this invention can contain as optional ingredients any of the various adjuvants which are ordinarily utilized in the production of pharmaceutical preparations. Thus, for example, in formulating dosage forms for oral administration, one may use as optional ingredients: fillers such as coprecipitated aluminum hydroxide-calcium carbonate, calcium phosphate dibasic, mannitol, lactose and the like; disintegrating agents such as maize starch, cellulose and the like; pharmaceutical tabletting lubricants such as talc, calcium stearate, magnesium stearate or the like; and acidifying agents which act to stabilize the preparations such as edible organic acids, for example, citric acid, tartaric acid and the like. Further, in forming liquid dosage forms of the compositions of the invention one may utilize conventional pharmaceutical adjuvants and carriers materials recognized as being conventional for preparation of such dosage forms such as, for example, water, sugar solutions, vegetable oils such as arachis oil and the like. The preparations of the invention may also contain other optional ingredients which are conventional in the art of pharmaceutical compounding such as suspending agents, sweeteners, preservatives, stabilizers, flavoring agents and the like. Such preparations may also be admitted to pharmaceutical expedients such as, for example, sterilization and the like.

The novel therapeutic compositions provided by the present invention are particularly advantageous in that, in addition to their antidepressive activity, they are effective in relieving severe insomnia. This combination of activities is particularly advantageous in the treatment of the depression syndrome since the normalizing of the sleep pattern to a substantial degree contributes toward improving the state of mind of the patient so that the therapeutic antidepressant activity of the preparation is maximized.

In accordance with a preferred embodiment of the present invention, dosage units containing L-5-hydroxy-tryptophan and $N^1$-(D,L-seryl)-$N^2$-(2,3,4-trihydroxybenzyl)-hydrazine are administered enterally, i.e. orally and rectally. Such dosage units contain from about 25 mg. to about 250 mg. of L-5-hydroxy-tryptophan or the equivalent amount of a pharmaceutically acceptable salt thereof and from about 25 mg. to about 250 mg. of $N^1$-(D,L-seryl)-$N^2$-(2,3,4-trihydroxybenzyl)-hydrazine or the equivalent amount of a pharmaceutically acceptable acid addition salt thereof. Generally, a daily dosage of a composition of the invention comprises from about 25 mg. to about 1,000 mg., preferably from about 50 mg. to about 750 mg. L-5-hydroxy-tryptophan and from about 100 mg. to about 500 mg. preferably from about 200 mg. of about 400 mg. of $N^1$-(D,L-seryl)-$N^2$-(2,3,4-trihydroxybenzyl)-hydrazine or the equivalent amounts of their pharmaceutical salts. This dosage is expediently divided equally over the course of the day, usually in three doses. Such doses and schedules therefor are determined by the clinician according to the individual therapeutic situation. While it is preferred in accordance with the present invention to administer L-5-hydroxy-tryptophan and $N^1$-(D,L-seryl)-$N^2$-(2,3,4-trihydroxybenzyl)-hydrazine in one dosage form thereby simplifying the effective control of the medication, it is possible to administer the two therapeutic agents separately in individual dosage forms without detracting from the therapeutic effect of the combination.

Patients suffering from depression are known to have an insufficient level of serotonin in the brain. Therefore, the following experiment which measures brain serotonin level demonstrates the antidepressant activity of the composition of the present invention. Three groups of rats were treated as follows: one group (the controls) received no medication, the second group received 225 mg/kg DL-5-hydroxy-tryptophan equivalent to about 112.5 mg/kg L-5-hydroxy-tryptophan i.p., the third group received 50 mg/kg $N^1$-(D,L-seryl)-$N^2$-(2,3,4-trihydroxybenzyl)hydrazine and the fourth group received 50 mg/kg $N^1$-(D,L-seryl)-$N^2$-(2,3,4-trihydroxybenzyl)-hydrazine i.p. followed after 30 minutes by 225 mg/kg DL-5-hydroxy-tryptophan i.p. The test animals with controls were decapitated two hours after injection of the DL-5-hydroxy-tryptophan and the serotonin content of the brain in µg/g of tissue was measured spectofluorimetrically. Additional groups of animals receiving varying dosages of L-5-hydroxy-tryptophan and $N^1$-(D,L-seryl)-$N^2$-(2,3,4-trihydroxybenzyl)-hydrazine individually and in combination separated by a 30 minute interval were treated as above. The results of these experiments are reported in Table I wherein L-5-hydroxy-tryptophan is designated as Compound A and $N^1$-(D,L-seryl)-$N^2$-(2,3,4-trihydroxybenzyl)-hydrazine is designated as Compound B.

Table I

| Medication mg/kg Cmpd. A | Cmpd. B | Ratio A:B | µg Serotonin | Deviation from Control |
|---|---|---|---|---|
| | | Control I | 0.368±0.03 | |
| approx. 112.5 | | | 0.890±0.04 | +0.522 |
| | 50 | | 0.350±0.01 | −0.018 |
| approx. 112.5 | 50 | approx. 2:1 | 1.110±0.06 | +0.742 |
| 50 | | | 0.595±0.017 | +0.227 |
| | 66 | | 0.342±0.006 | −0.026 |
| 50 | 66 | approx. 1:1 | 0.865±0.006 | +0.497 |
| | | Control II* | 0.417±0.006 | |
| 20 | | | 0.468±0.011 | +0.051 |
| 20 | 100 | 1:5 | 0.558±0.007 | +0.09 |
| 100 | | | 1.175±0.038 | +0.758 |
| 100 | 50 | 2:1 | 1.558±0.067 | +1.141 |

*the results following were compared against a second set of controls

The results of the above experiments clearly illustrate the substantial increase in brain serotonin content resulting from the administration of L-5-hydroxy-tryptophan as well as the substantial increase in the activity thereof by the concurrent administration of $N^1$-(D,L-seryl)-$N^2$-(2,3,4-trihydroxybenzyl)-hydrazine.

The ability of $N^1$-(D,L-seryl)-$N^2$-(2,3,4-trihydroxybenzyl)-hydrazine to prevent the occurrence of an undesirable increase in blood pressure following the administration of L-5-hydroxy-tryptophan is demonstrated by the following test on dogs narcotized with choralose. In this test, L-5-hydroxy-tryptophan was administered, followed by $N^1$-(D,L-seryl)-$N^2$-(2,3,4-trihydroxybenzyl)-hydrazine, followed by a second administration of L-5-hydroxy-tryptophan. During the test, readings were taken as follows: pressure in the A. pulmonalis; pressure in the systemic arterial circulation; and heart frequency. The procedure as well as the data collected are set forth in Table II. Dog No. 1 weighed 11 kg. and Dog No. 2 weighed 7 kg.

Table II

| Sequential Procedure | pressure in A. pulmonalis, mm Hg | | pressure in arterial circulation, mm Hg | | heart frequency per minute | |
|---|---|---|---|---|---|---|
| | Dog No. 1 | Dog No. 2 | Dog No. 1 | Dog No. 2 | Dog No. 1 | Dog No. 2 |
| Before start of infusion | 23/5 | 25/5 | 140/90 | 140/100 | 120 | 120 |
| Infusion of L-5-hydroxy-tryptophan, 4 mg/min during 15 minutes | 30/8 | 32/5 | 170/110 | 160/110 | 140 | 130 |
| 45 Minutes after end of infusion | 20/5 | 27/5 | 145/90 | 160/110 | 120 | 120 |
| Infusion of $N^1$-(D,L-seryl)-$N^2$-(2,3,4-trihydroxybenzyl)-hydrazine (100 mg/kg in 15 minutes) | 25/5 | 40/5 | 160/110 | 210/135 | 110 | 120 |
| 15 Minutes after end of infusion | 25/5 | 30/5 | 160/100 | 180/120 | 110 | 115 |
| Infusion of L-5-hydroxy-tryptophan (4 mg/min during 22 | | | | | | |

Table II-continued

| Sequential Procedure (minutes) | pressure in A. pulmonalis, mm Hg | | pressure in arterial circulation, mm Hg | | heart frequency per minute | |
|---|---|---|---|---|---|---|
| | Dog No. 1 | Dog No. 2 | Dog No. 1 | Dog No. 2 | Dog No. 1 | Dog No. 2 |
| | 24/4 | 26/5 | 140/100 | 170/120 | 110 | 115 |

The results given in the table establish that the presence of N¹-(D,L-seryl)-N²-(2,3,4-trihydroxybenzyl)-hydrazine prevents the blood pressure increase, particularly in the A. pulmonalis which occurs after the infusion of L-5-hydroxy-tryptophan. It is therefore apparent that N¹-(D,L-seryl)-N²-(2,3,4-trihydroxy-benzyl)-hydrazine can prevent this serious side effect of L-5-hydroxy-tryptophan. Throughout the foregoing experiment, the heart frequency of each dog remained practically uninfluenced.

The following experiment was conducted to demonstrate the fact that the compositions of the present invention are non-toxic. Each member of a group of 8 male and 8 female rats was treated five times weekly over a period of 13 weeks with a single daily dose of 200 mg/kg L-5-hydroxy-tryptophan and 100 mg./kg. N¹-(D,L-seryl)-N²-(2,3,4-trihydroxybenzyl)-hydrazine. In comparison with control rats receiving no medication, no charge was noted in the general condition or weight development of the experimental animals. Hematological and histological investigations of the experimental animals also showed no differences from the control rats receiving no medication.

The following examples further illustrate the invention.

EXAMPLE 1

A homogeneous mixture was formed from 125 parts by weight of N¹-(D,L-seryl)-N²-(2,3,4-trihydroxybenzyl)-hydrazine hydrochloride, 50 parts by weight of L-5-hydroxytryptophan, 5 parts by weight citric acid and 255 parts by weight microcrystalline cellulose. The resulting powder mixture was wet granulated with 60 parts by weight maize starch as a 10% by weight aqueous solution. The resulting granulation was sieved, combined with 5 parts by weight magnesium stearate, homogenized and pressed into tablets each of which weighed 500 mg. Each tablet had the following composition:

| Ingredient | Amount | |
|---|---|---|
| N¹-(D,L-seryl)-N²-(2,3,4-trihydroxybenzyl)-hydrazine hydrochloride | | 125 mg. |
| L-5-hydroxy-tryptophan | | 50 mg. |
| Citric Acid | | 5 mg. |
| Microcrystalline Cellulose | | 255 mg. |
| Maize Starch | | 60 mg. |
| Magnesium Stearate | | 5 mg. |
| | Total | 500 mg. |

EXAMPLE 2

Tablets having the following composition were prepared in accordance with the manner described in Example 1:

| Ingredient | Amount |
|---|---|
| N¹-(D,L-seryl)-N²-(2,3,4-trihydroxybenzyl)-hydrazine hydrochloride | 100 mg. |
| L-5-hydroxy-tryptophan | 100 mg. |
| Citric Acid | 5 mg. |
| Microcrystalline Cellulose | 230 mg. |
| Maize Starch | 60 mg. |
| Magnesium Stearate | 5 mg. |
| Total | 500 mg. |

EXAMPLE 3

A total of 142.5 parts by weight N¹-(D,L-seryl)-N²-(2,3,4-trihydroxybenzyl)-hydrazine hydrochloride, 50 parts by weight L-5-hydroxytryptophan and 102.5 parts by weight mannitol were homogeneously blended and sieved. The resulting powder mixture was wet granulated with 250 parts by weight of a 2% by weight solution of polyvinylpyrrolidone in methyl chloride. The resulting granulation was sieved, combined with 1.5 parts by weight magnesium stearate and 18.5 parts by weight talc and homogeneously blended. The mixture was then filled into number O capsules, each capsule containing the following composition:

| Ingredient | Amount | |
|---|---|---|
| N¹-(D,L-seryl)-N²-(2,3,4-trihydroxybenzyl)-hydrazine hydrochloride | 142.5 | mg. |
| L-5-hydroxy-tryptophan | 50 | mg. |
| Mannitol | 102.5 | mg. |
| Polyvinylpyrrolidone | 5 | mg. |
| Magnesium Stearate | 1.5 | mg. |
| Talc | 18.5 | mg. |
| Total | 325 | mg. |

I claim:

1. A therapeutic composition for the treatment of depression and insomnia comprising a therapeutically inert, pharmaceutically acceptable carrier material, and as an active ingredient from about one part to about four parts by weight L-5-hydroxy-tryptophan or the equivalent amount of a pharmaceutically acceptable salt thereof and from one part to about five parts by weight N¹-(D,L-seryl)-N²-(2,3,4-trihydroxybenzyl)-hydrazine or the equivalent amount of a pharmaceutically acceptable acid addition salt thereof.

2. The composition of claim 1 wherein said active ingredient comprises about four parts by weight L-5-hydroxy-tryptophan or the equivalent amount of a pharmaceutically acceptable salt thereof and about one part by weight of N¹-(D,L-seryl)-N²-(2,3,4-trihydroxybenzyl)-hydrazine or the equivalent amount of a pharmaceutically acceptable acid addition salt thereof.

3. The composition of claim 1 wherein said active ingredient comprises about two parts by weight L-5-hydroxy-tryptophan or the equivalent amount of a pharmaceutically acceptable salt thereof and about one part by weight of N¹-(D,L-seryl)-N²-(2,3,4-trihydroxybenzyl)-hydrazine or the equivalent amount of a pharmaceutically acceptable acid addition salt thereof.

4. The composition of claim 1 wherein said active ingredient comprises about one part by weight of L-5-hydroxy-tryptophan or the equivalent amount of a pharmaceutically salt thereof for each part by weight of $N^1$-(D,L-seryl)-$N^2$-(2,3,4-trihydroxybenzyl)-hydrazine or the equivalent amount of a pharmaceutically acceptable acid addition salt thereof.

5. The composition of claim 1 in unit dosage form suitable for enteral administration each such unit dosage form containing from about 25 mg. to about 250 mg. of L-5-hydroxy-tryptophan or an equivalent amount of a pharmaceutically acceptable salt thereof and from about 25 mg. to about 250 mg. of $N^1$-(D,L-seryl)-$N^2$-(2,3,4-trihydroxybenzyl)-hydrazine or the equivalent amount of a pharmaceutically acceptable acid addition salt thereof.

6. A method for the treatment of depression and insomnia which comprises administering to a patient in need of such treatment an effective amount of the composition of claim 1.

7. A method for the treatment of depression and insomnia which comprises administering to a patient in need of such treatment an effective amount of the composition of claim 2.

8. A method for the treatment of depression and insomnia which comprises administering to a patient in need of such treatment an effective amount of the composition of claim 3.

9. The method of claim 6 wherein the daily dosage of said composition administered to said patient comprises from about 25 mg. to about 1,000 mg. of L-5-hydroxy-tryptophan or the equivalent amount of a pharmaceutically acceptable salt thereof, and from about 100 mg. to about 500 mg. of $N^1$-(D,L-seryl)-$N^2$-(2,3,4-trihydroxybenzyl)-hydrazine or an equivalent amount of a pharmaceutically acceptable acid addition salt thereof.

10. The method of claim 6 wherein the daily dosage of said composition administered to said patient comprises from about 50 mg. to about 750 mg. of L-5-hydroxy-tryptophan or an equivalent amount of a pharmaceutically acceptable salt thereof, and from about 200 mg. to about 400 mg. of $N^1$-(D,L-seryl)-$N^2$-(2,3,4-trihydroxybenzyl)-hydrazine or an equivalent amount of a pharmaceutically acceptable acid addition salt thereof.

* * * * *